United States Patent [19]

Watts

[11] Patent Number: 4,569,940

[45] Date of Patent: Feb. 11, 1986

[54] CERTAIN 5-N-MONO- OR DISUBSTITUTED SULFAMOYL BENZAMIDES HAVING USE IN TREATMENT OF EMESIS, IMPAIRED GASTRO-INTESTINAL MOTILITY DISORDERS AND CENTRAL NERVOUS SYSTEM DISORDERS

[75] Inventor: Eric A. Watts, Harlow, England

[73] Assignee: Beecham Group P.L.C., Brentford, England

[21] Appl. No.: 500,850

[22] Filed: Jun. 3, 1983

[30] Foreign Application Priority Data

Jun. 4, 1982 [GB] United Kingdom ............... 8216372

[51] Int. Cl.[4] ................... C07D 451/04; A61K 31/46
[52] U.S. Cl. ................................... 514/304; 546/124; 546/125
[58] Field of Search ............... 546/124, 125; 424/265; 514/304

[56] References Cited

U.S. PATENT DOCUMENTS

4,273,778  6/1981  Hadley et al. ...................... 514/304

FOREIGN PATENT DOCUMENTS

0013138  7/1980  European Pat. Off. ............ 546/124
0042705  12/1981  European Pat. Off. ............ 546/124

OTHER PUBLICATIONS

P. Protais, J. Constentin, and J. C. Schwartz, "Climbing Behavior Induced by Apomorphine in Mice: a Simple Text for the Study of Dopamine Receptors in Striatum", Psychopharmacology 50, 1976, pp. 1–6.

*Primary Examiner*—Alan L. Rotman
*Attorney, Agent, or Firm*—James F. Haley, Jr.; Paul H. Ginsburg

[57] ABSTRACT

Compounds of formula (I):

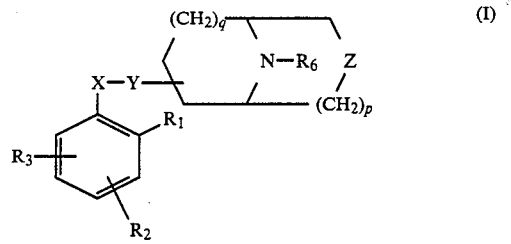

wherein:
one of X and Y is CO and the other is NH;
$R_1$ is $C_{1-6}$ alkoxy or $C_{1-6}$ alkylthio;
$R_2$ is hydrogen, trifluoromethyl, $C_{1-6}$ alkylthio, $C_{1-7}$ acyl, $C_{1-7}$ acylamino, $C_{1-6}$ alkylsulphonyl, $C_{1-6}$ alkylsulphinyl, halogen, nitro or amino, aminocarbonyl or aminosulphonyl optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by one or more halogen, trifluoromethyl, $C_{1-6}$ alkoxy or nitro groups, or N-disubstituted by $C_{2-5}$ polymethylene;
$R_3$ is amino, aminocarbonyl or aminosulphonyl N-substituted by one or two $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by one or more halogen, trifluoromethyl, $C_{1-6}$ alkoxy or nitro groups, or N-disubstituted by $C_{1-6}$ alkyl and one of the foregoing list of N-substituents or $C_{4-5}$ polymethylene;
$R_6$ is $C_{1-7}$ alkyl, —$(CH_2)_s R_7$, s being 0 to 2 and $R_7$ being $C_{3-8}$ cycloalkyl, —$(CH_2)_t R_8$, t being 1 or 2 and $R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolyzable acyloxy;
Z is $CH_2$ or oxygen;
p and q are independently 0 to 2 when X is $CH_2$ and are both 1 when Z is oxygen, having dopamine antagonist activity, a process for their preparation and their use as pharmaceuticals.

12 Claims, No Drawings

CERTAIN 5-N-MONO- OR DISUBSTITUTED SULFAMOYL BENZAMIDES HAVING USE IN TREATMENT OF EMESIS, IMPAIRED GASTRO-INTESTINAL MOTILITY DISORDERS AND CENTRAL NERVOUS SYSTEM DISORDERS

This invention relates to novel compounds, to pharmaceutical compositions containing them, and to a process for their preparation.

European Patent Application No. 79302978.6 and U.S. Pat. No. 4273778 disclose that compounds of the formula (A), and pharmaceutically acceptable salts thereof:

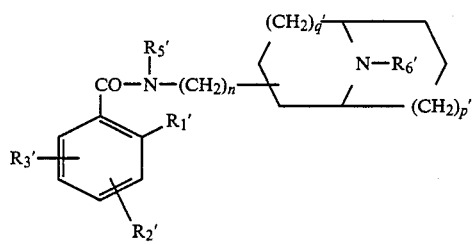

wherein:

$R_1'$ is a $C_{1-6}$ alkoxy group;

$R_2'$ and $R_3'$ are the same or different and are hydrogen, halogen, $CF_3$, $C_{2-7}$ acyl, $C_{2-7}$ acylamino, or amino, aminocarbonyl or aminosulphone optionally substituted by one or two $C_{1-6}$ alkyl groups, $C_{1-6}$ alkylsulphone or nitro;

$R_5'$ is hydrogen or $C_{1-6}$ alkyl;

$R_6'$ is $C_{1-7}$ alkyl or a group $—(CH_2)_s R_7'$ where $s'$ is 0 to 2 and $R_7'$ is a $C_{3-8}$ cycloalkyl group, or a group $—(CH_2)_{t'} R_8'$ where $t'$ is 1 or 2 and $R_8'$ is $C_{2-5}$ alkenyl or a phenyl group optionally substituted by one or two substituents selected from $C_{1-6}$ alkyl, $C_{1-4}$ alkoxy, trifluoromethyl and halogen; and $n'$, $p'$ and $q'$ are independently 0 to 2; have useful pharmacological activity. More specifically the compounds of formula (A) are stated to be useful in the treatment of disorders related to impaired gastro-intestinal motility and/or in the treatment of disorders of the central nervous system. All the compounds are stated to have anti-emetic activity.

The said European Application and U.S. Patent, the subject matter of which is imported herein by reference, has extensive exemplification of typical compounds of the formula (A) and of their pharmacological activity, establishing the veracity of the claimed utilities for the class of compounds defined by formula (A).

It has now been found that certain compounds of a structure distinct from that of formula (A) also have a useful pharmacological activity, namely dopamine antagonist activity.

Accordingly the present invention provides a compound of formula (I) or a pharmaceutically acceptable salt and/or solvate and/or N-oxide thereof:

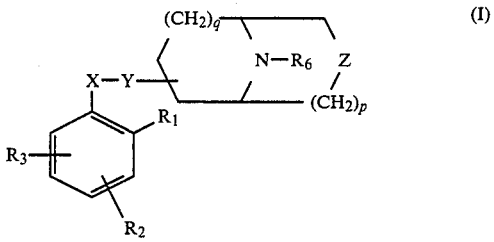

wherein:

one of X and Y is CO and the other is NH;

$R_1$ is $C_{1-6}$ alkoxy or $C_{1-6}$ alkylthio;

$R_2$ is hydrogen, trifluoromethyl, $C_{1-6}$ alkylthio, $C_{1-7}$ acyl, $C_{1-7}$ acylamino, $C_{1-6}$ alkylsulphonyl, $C_{1-6}$ alkylsulphinyl, halogen, nitro or amino, aminocarbonyl or aminosulphonyl optionally N-substituted by one or two groups selected from $C_{1-6}$ alkyl, $C_{3-8}$ cycloalkyl, $C_{3-8}$ cycloalkyl $C_{1\alpha 4}$ alkyl, phenyl or phenyl $C_{1-4}$ alkyl groups any of which phenyl moieties may be substituted by one or more halogen, trifluoromethyl, $C_{1-6}$ alkoxy or nitro groups, or N-disubstituted by $C_{2-5}$ polymethylene;

$R_3$ is amino, aminocarbonyl or aminosulphonyl N-substituted by one or two $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by or more halogen, trifluoromethyl, $C_{1-6}$ alkoxy or nitro groups, or N-disubstituted by $C_{1-6}$ alkyl and one of the foregoing list of N-substituents or $C_{4-5}$ polymethylene;

$R_6$ is $C_{1-7}$ alkyl, $—(CH_2)_s R_7$, s being 0 to 2 and $R_7$ being $C_{3-8}$ cycloalkyl, $—(CH_2)_t R_8$, t being 1 or 2 and $R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolysable acyloxy;

Z is $CH_2$ or oxygen;

p and q are independently 0 to 2 when X is $CH_2$ and are both 1 when Z is oxygen.

Favourably X is CO and Y is NH.

Suitable examples of the group $R_1$ include methoxy, ethoxy, n- and iso-propoxy, methylthio, ethylthio and n- and iso-propylthio.

Preferably $R_1$ is methoxy.

Suitable examples of $R_2$ include the following groups: hydrogen, chlorine, bromine, amino, $C_{1-4}$ alkanoylamino such as formylamino, acetylamino, propionylamino, n- and iso-butyrylamino, aminosulphonyl, and amino and aminosulphonyl substituted by one or two methyl, ethyl, n- or iso-propyl, n-, sec- or tert-butyl groups, cyclohexyl, cyclopentyl, phenyl or benzyl groups or N-disubstituted by $C_2$, $C_3$, $C_4$ or $C_5$ polymethylene, nitro, methylthio, ethylthio, n- and iso-propylthio.

Preferably $R_2$ is hydrogen, chloro or amino.

Often, $R_2$ is hydrogen.

It is generally preferred that $R_2$ is in the 4-position relative to the bicycloalkyl acylamino side chain for greater activity in the resultant compound of the formula (I). For the same reason it is generally preferred that $R_3$ is in the 5-position relative to the same acylamino side chain.

Suitable examples of $R_3$ N-substituents include cyclobutyl, cyclopentyl, cyclohexyl, cycloheptyl; cyclopropylmethyl, phenyl, cyclobutylmethyl, cyclopentylmethyl, cyclohexylmethyl, methyl, ethyl, n- and iso-propyl and disubstituted by $C_2$, $C_3$, $C_4$ or $C_5$ polymethylene.

Often, $R_3$ N-substituents are other than $C_{1-6}$ alkyl.

Preferred values for $R_3$ include aminosulphonyl N-monosubstituted by cyclopentyl, phenyl or benzyl or N-disubstituted by $C_3$, $C_4$ or $C_5$ polymethylene.

Most preferably, $R_3$ is aminosulphonyl N-disubstituted by trimethylene.

Y and the nitrogen atom of the bicyclic ring system are separated by two or three carbon atoms. A separation of three carbon atoms is preferred.

When the separation is 3 atoms the X—Y moiety is preferably in an equatorial orientation to the bicyclic system.

Suitable examples of $R_6$, when $C_{1-7}$ alkyl, include methyl, ethyl, n- and iso-propyl and n-, iso-, sec- and tert-butyl. Within $C_{1-7}$ alkyl, $C_{5-7}$ alkyl are of interest and examples thereof include n-pentyl, n-hexyl, n-heptyl 3-methylbutyl, 2,2-dimethylpropyl and 3,3-dimethylbutyl.

Suitable examples of $R_6$, when —$(CH_2)_s R_7$ are those wherein s is 1, in particular those wherein $R_7$ is $C_{5-8}$ cycloalkyl, such as cyclohexyl.

Suitable examples of $R_6$ when —$(CH_2)_t R_8$ are those wherein t is 1. $R_8$ may be 2- or 3-thienyl or preferably is phenyl optionally substituted by hydrogen, $C_{1-4}$ alkoxy, trifluoromethyl, halogen, carboxy, esterified carboxy or $C_{1-4}$ alkyl optionally substituted by hydroxy, $C_{1-4}$ alkoxy, carboxy, esterified carboxy and in vivo hydrolysable acyloxy.

When p is 0 and $R_6$ is —$(CH_2)_t R_8$, t is preferably 1 and $R_8$ is preferably unsubstituted phenyl.

When p is 1 and $R_6$ is —$(CH_2)_t R_8$, t is preferably 1 and $R_8$ is preferably monosubstituted phenyl, in particular mono-p-substituted phenyl. Examples of preferred p-substituents include methyl, trifluoromethyl, fluoro, chloro and bromo, especially fluoro. p-Fluoro-benzyl, p-chlorobenzyl and p-methylbenzyl are especially preferred examples of $R_6$ when p is 1.

When phenyl is substituted by optionally substituted $C_{1-4}$ alkyl, suitable examples of $C_{1-4}$ alkyl include methyl, ethyl, n- and iso-propyl, and n-, iso-, sec- and tert-butyl; methyl however, is preferred. Examples of substituents of such alkyl groups include hydroxy, methoxy, ethoxy, n- and iso-propoxy, carboxy, esterified carboxy, and in vivo hydrolysable acyloxy. The substitution preferably occurs on the terminal carbon atom of the alkyl group.

Examples of esterified carboxy groups include $C_{1-4}$ alkoxycarbonyl, such as methoxy-, ethoxy-, n- and iso-propoxy-carbonyl, phenoxycarbonyl or benzyloxycarbonyl, either being optionally substituted in the phenyl ring by one or two substituents selected from $C_{1-4}$ alkyl, $C_{1-4}$ alkoxy, trifluoromethyl, halogen or nitro.

Examples of in vivo hydrolysable acyloxy groups include $C_{2-6}$ alkanoyloxy, for examples acetoxy, propionoxy, n- and iso-butyroxy, and 2,3 dimethylpropanyloxy, benzyloxy or benzenesulphonyloxy either being optionally substituted in the phenyl ring by one or two substituents selected from $C_{1-4}$ alkyl, $C_{1-4}$ alkoxy, trifluoromethyl, halogen or nitro, or sulphonyloxy groups, for example $C_{1-6}$ alkanesulphonyloxy group, such as methanesulphonyloxy.

Z is preferably $CH_2$.

There is a group of compounds within formula (I) wherein $R_2$ is hydrogen, trifluoromethyl, $C_{1-6}$ alkylthio, $C_{1-7}$ acyl, $C_{1-7}$ acylamino, $C_{1-6}$ alkylsulphonyl, $C_{1-6}$ alkylsulphinyl, halogen, nitro or amino, aminocarbonyl or aminosulphonyl optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by one or more halogen, trifluoromethyl, $C_{1-6}$ alkoxy or nitro groups, or N-disubstituted by $C_{4-5}$ polymethylene; and the remaining variables are as defined in formula (I).

The pharmaceutically acceptable salts of the compounds of this invention include acid addition salts with conventional acids such as hydrochloric, hydrobromic, phosphoric, sulphuric, citric, tartaric, lactic and acetic acid, and quaternary ammonium salts with alkyl, phenalkyl and cycloalkyl halides. Suitable examples of such quaternising agents include methyl, ethyl, n- and iso-propyl, benzyl, phenethyl chlorides, bromides and iodides.

Examples of pharmaceutically acceptable salts also include internal salts such as N-oxides.

The compounds of the formula (I) can also form hydrates, and the invention extends to such hydrates.

From the aforesaid it will be appreciated that favourably the benzamide or anilide moiety is of formula (II):

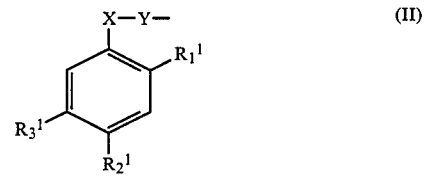

wherein:

$R_1^1$ is $C_{1-6}$ alkoxy;

$R_2^1$ is hydrogen, chloro, amino or $C_{1-4}$ alkanoylamino; and $R_3^1$ is aminosulphonyl N-substituted or N-disubstituted as defined in formula (I).

A preferred group of compounds within those of formula (I), are those of formula (III):

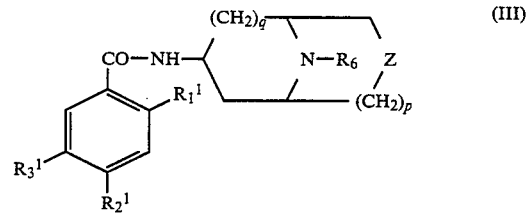

wherein $R_1^1$, $R_2^1$, $R_3^1$, Z, p and q are as defined in formulae (I) and (II).

More suitably p is 0 or 1, preferably 0, when Z is $CH_2$, or 1 when Z is 0. Preferably q is 1 and the moiety of formula (II) is then attached at the 3-position numbering through the $(CH_2)_q$-containing ring from a bridgehead atom taken as 1 (not necessarily standard numbering).

Suitable and preferred examples of $R_6$ in formula (III) include those listed under formula (I) for $R_6$.

Preferably $R_1^1$ is methoxy.

Suitable values for $R_3^1$ when $C_{1-4}$ alkanoylamino include formylamino and acetylamino.

$R_2^1$ is preferably hydrogen.

$R_3^1$ N-substituents are often other than $C_{1-6}$ alkyl.

$R_3{}^1$ is preferably aminosulphonyl monosubstituted by a cyclopentyl, cyclohexyl, or cycloheptyl group or N-disubstituted by trimethylene.

Most preferably $R_3{}^1$ is azetidinylaminosulphonyl.

A preferred sub-group of compounds within formula (III) is of formula (IV):

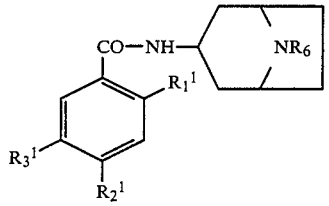

(IV)

wherein $R_1{}^1$, $R_2{}^1$, $R_3{}^1$ and $R_6$ are as defined in formulae (I) and (II).

Suitable and preferred values of $R_1{}^1$, $R_2{}^1$, $R_3{}^1$ and $R_6$ are as hereinbefore described in relation to formulae (I) and (II).

It is preferred that the CONH moiety is in the β-orientation to the nortropane ring, that is as follows:

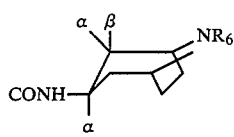

(The 2α and 2β orientations are also depicted)

A further sub-group of compounds within formula (III) is of formula (V):

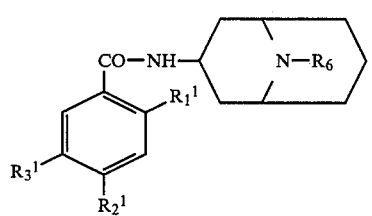

(V)

wherein $R_1{}^1$, $R_2{}^1$, $R_3{}^1$ and $R_6$ are as defined in formulae (I) and (II).

Suitable and preferred values of $R_1{}^1$, $R_2{}^1$, $R_3{}^1$, and $R_6$ are as described in relation to formulae (I) and (II).

It is preferred that the CONH moiety is in the β-orientation to the granatane ring, the β-orientation being the same as in the nortropane hereinbefore depicted.

A sub-group of compounds within those of formula (III) are those of the formula (VI):

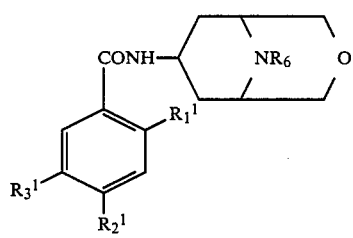

(VI)

wherein $R_1{}^1$, $R_2{}^1$, $R_3{}^1$ and $R_6$ are as hereinbefore defined.

It is preferred that the CONH moiety is in the β-orientation to the oxagranatane ring, that is as follows:

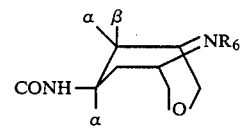

(The 6α and 6β-orientation are also depicted).

Within each of formulae (II) to (VI) are sub-groups of compounds, wherein $R_6$ is $C_{1-7}$ alkyl such as $C_{5-7}$ alkyl, 2-thienylmethyl or $-(CH_2)_t R_8$, t being 1 or 2 and $R_8$ being phenyl optionally substituted by one or two substituents selected from $C_{1-4}$ alkoxy, trifluoromethyl, halogen, carboxy, esterified carboxy, and $C_{1-4}$ alkyl optionally substituted by hydroxy, $C_{1-4}$ alkoxy, carboxy, esterified carboxy or in vivo hydrolysable acyloxy.

Within each of these latter sub-groups, there are compounds within formulae (II) to (VI) respectively, wherein $R_6$ is $C_{5-7}$ alkyl.

Within each of these same sub-groups, there are compounds within formulae (II) to (VI) respectively, wherein $R_6$ is cyclohexylmethyl, 2-thienylmethyl or $-(CH_2)_t R_8$, t being 1 or 2 and $R_8$ being phenyl optionally substituted by one or two substituents selected from $C_{1-4}$ alkoxy, trifluoromethyl, halogen, carboxy, esterified carboxy, and $C_{1-4}$ alkyl optionally substituted by hydroxy, $C_{1-4}$ alkoxy, carboxy, esterified carboxy or in vivo hydrolysable acyloxy.

Particularly preferred compounds within formula (IV) are those wherein $R_6$ is unsubstituted benzyl.

Favourable compounds within formula (V) and (IV) are those wherein $R_6$ is benzyl optionally substituted in the phenyl ring by one or two substituents selected from $C_{1-4}$ alkoxy, trifluoromethyl, halogen and $C_{1-4}$ alkyl.

It is preferred in formula (V) that the phenyl ring is monosubstituted and/or that the substitution is in the para-position and/or that the substituent is chloro, fluoro or methyl.

$R_6$ is formula (V) is most preferably p-methylbenzyl, p-chlorobenzyl and particularly p-fluorobenzyl.

Particularly suitable examples of the compounds of the present invention include those of the Examples hereinafter.

It will of course be realised that the compounds of the formula (I) have chiral or prochiral centres, and thus are capable of existing in a number of stereoisomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The invention also provides a process for the preparation of a compound of the formula (I), which process comprises reacting a compound of the formula (VII):

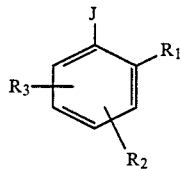

with a compound of formula (VIII):

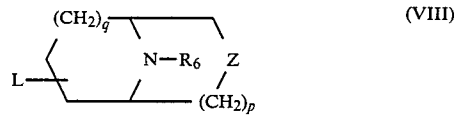

wherein:
one of J and L is COQ$_1$, where Q$_1$ is a leaving group, and the other is —NH$_2$; and the remaining variables are as defined in formula (I), with the proviso that when J is —NH$_2$, R$_2$ or R$_3$ is other than amino; and thereafter optionally converting R$_2$ to R$_3$ to another R$_2$ or R$_3$ respectively; as necessary converting R$_6$ to other R$_6$; and optionally forming a pharmaceutically acceptable salt of the resultant compound of the formula (I).

The leaving group Q$_1$ is a group that is readily displaceable by a nucleophile. Examples of such groups are hydroxy, halogen such as chloro and bromo.

If the leaving group is hydroxy, then the reaction is preferably carried out in an inert non-hydroxylic solvent, such as benzene, toluene or diethyl ether in the presence of a dehydrating catalyst, such as a carbodiimide, for example dicyclohexylcarbodiimide. The reaction may be carried out at a non-extreme temperature such as −10° to 100° C., for example 0° to 80° C.

If the leaving group is a halide, then the reaction is preferably carried out at a non-extreme temperature in an inert non-hydroxylic solvent, such as benzene, toluene or diethyl ether. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate.

If the leaving group is acyloxy, then the reaction is preferably carried out in substantially the same manner as if the leaving group were hydroxy. Suitable examples of acyloxy leaving groups include C$_{1-4}$alkanoyloxy, mesyloxy, tosyloxy and triflate.

If the leaving group is C$_{1-4}$ alkoxycarbonyloxy, then the reaction is preferably carried out in an inert solvent, such as methylene chloride, at a non-extreme temperature in the presence of an acid acceptor, such as triethylamine.

If the leaving group is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

The compounds of formula (VII) and (VIII) are either known compounds or can be prepared analogously to the preparation of structurally similar known compounds.

Compounds of formula (VII) wherein R$_3$ is aminosulphonyl may be formed from the corresponding chlorosulphonyl derivatives of the compound of formula (VII) wherein R$_3$ is replaced by hydrogen, with a suitable amine and ammonia.

The skilled man will appreciate that the choice or necessity of conversion of groups R$_2$ and/or R$_3$ to other groups R$_2$ and/or R$_3$ will be dictated by the nature and position of substituents R$_1$, R$_2$ and R$_3$.

It will be apparent that compounds of the formula (I) containing an R$_2$, R$_3$ or R$_6$ group which is convertible to another R$_2$ and R$_3$ group or to an R$_6$ group are useful novel intermediates. A number of such conversions is possible not only for the end compounds of formula (I), but also for their intermediates as follows:

(a) an hydrogen substituent is convertible to a nitro substituent by nitration;

(b) a nitro substituent is convertible to an amino substituent by reduction;

(c) a C$_{1-4}$ acylamino substituent is convertible to an amino substituent by deacylation;

(d) an amino substituent is convertible to a C$_{1-4}$ acylamino substituent by acylation;

(e) a hydrogen substituent is convertible to a halogen substituent by halogenation; and (f) a C$_{1-6}$ alkylthio or C$_{1-6}$ alkylsulphinyl substituent is convertible to a C$_{1-6}$ alkylsulphinyl or a C$_{1-6}$ alkylsulphonyl substituent respectively by oxidation.

Conversions (a) to (f), are only exemplary and are not exhaustive of the possibilities.

In regard to (a), nitration is carried out in accordance with known procedures.

In regard to (b), the reduction is carried out with a reagent suitable for reducing nitroanisole to aminoanisole.

In regard to (c), deacylation is carried out by treatment with a base, such as an alkali metal hydroxide.

In regard to (d), the acylation is carried out with an acylating agent, such as the corresponding acid or acid chloride. Formylation is carried out with the free acid.

In regard to (e), halogenation is carried out with conventional halogenating agents.

In regard to (f), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide.

It will be appreciated that, R$_6$ when optionally substituted benzyl as hereinbefore defined, may be replaced by another group R$_6$.

Such R$_6$ benzyl groups may be removed for example when R$_2$ or R$_3$ is not halogen by conventional transition metal catalysed hydrogenolysis to give compounds of the formula (X):

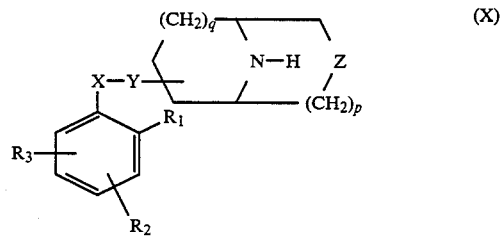

wherein the variable groups are as defined in formula (I).

This invention also provides an optional process step in the preparation of a compound of the formula (I) which comprises the reaction of a corresponding compound of the formula (X) as hereinbefore defined with a compound $Q_2R_6$ wherein $R_6$ is as defined in formula (I) and $Q_2$ is a leaving group, and optionally forming a pharmaceutically acceptable salt of the resulting compound of the formula (I).

Suitable values for $Q_2$ include groups readily displaced by nucleophiles such as Cl, Br, I, $OSO_2CH_3$ or $OSO_2C_6H_4pCH_3$.

Favoured values for $Q_2$ include Cl, Br and I.

Particularly suitably the compound $Q_2R_6$ is a benzyl halide, such as the bromide or chloride.

The reaction may be carried out under conventional alkylation conditions for example in an inert solvent such as dimethylformamide in the presence of an acid acceptor such as potassium carbonate. Generally the reaction is carried out at non-extreme temperature such as at ambient or at a slightly elevated temperature.

Converting $R_6$ to another $R_6$ in the compound of the formula (VIII) before coupling with the compound of the formula (VII) or its derivative is preferred. Such interconversions are effected conveniently under the above conditions. It is desirable to protect the amine function with a group readily removable by acidolysis such as a $C_{2-7}$ alkanoyl group before $R_6$ interconversion.

The substituents in the phenyl ring when $R_6$ is benzyl in a compound of formula (I), in particular the substituted $C_{1-4}$ alkyl substituents, are interconvertible. A number of such interconversions are possible not only for the end compounds of formula (I), but also for their intermediates as follows:

(i) a carboxy $C_{1-4}$ alkyl substituent is convertible to an esterified carboxy $C_{1-4}$ alkyl substituent by esterification;

(ii) an esterified carboxy $C_{1-4}$ alkyl substituent is convertible to a carboxy $C_{1-4}$ alkyl substituent by deesterification;

(iii) $C_{1-4}$ alkoxy $C_{1-4}$ alkyl substituent or an in vivo hydrolysable $C_{2-4}$ acyloxy $C_{1-4}$ alkyl substituent is convertible to an hydroxy $C_{1-4}$ alkyl substituent;

(iv) an optionally esterified carboxy or carboxy $C_{1-3}$ alkyl substituent is convertible to an hydroxymethyl or hydroxy $C_{2-4}$ alkyl substituent by reduction; and (v) a hydroxy $C_{1-4}$ alkyl is convertible to $C_{1-4}$ alkyl by O-alkylation or to in vivo hydrolysable $C_{2-4}$ acyloxy $C_{1-4}$ alkyl by O-acylation.

Conversions (i) to (iv) are only exemplary and are not exhaustive of the possibilties.

In regard to (i) and (ii), the esterification and deesterification reactions are carried out in conventional manner.

In regard to (iii), a $C_{1-4}$ alkoxy $C_{1-4}$ alkyl substituent is convertible to an hydroxy $C_{1-4}$ alkyl substituent by conventional methods, such as warming with aqueous hydrobromic acid or by treatment with pyridine hydrochloride, boron tribromide, boron triodide or iodotrimethylsilane.

An in vivo hydrolysable $C_{2-4}$ acyloxy $C_{1-4}$ alkyl substituent is convertible to an hydroxy $C_{1-4}$ alkyl substituent by acid or base hydrolysis.

In regard to (iv), the reduction is carried out with a selective metal complex hydride, for example lithium aluminium hydride, under conventional conditions.

In regard to (v), O-alkylation is carried out under conventional conditions in an inert solvent at a non-extreme temperature such as ambient temperature or slightly above or at reflux temperature. The $C_{1-4}$ alkylating agent has a leaving group that is readily displaceable by a nucleophile. Examples of leaving groups include halide, such as chloride, bromide or iodide, or labile acyloxy groups, such as mesyl and tosyl.

O-acylation is carried out under conventional conditions with an acylating agent which has an acyl group capable of forming an in vivo hydrolysable acyloxy group and a leaving group, such as halide, for example chloride and bromide, and hydrogen. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

Compounds of the formula (X) are novel intermediates and thus form an aspect of the present invention.

It will be realised that in the compound of the formula (I) the -X-Y-linkage may have an $\alpha$ or $\beta$ orientation with respect to the ring of the bicyclic moiety to which it is attached. A mixture of $\alpha$ and $\beta$ isomers of the compound of the formula (I) may be synthesised non-stereospecifically and the desired isomer separated conventionally therefrom eg by chromatography; or alternatively the $\alpha$ and $\beta$ isomer may if desired be synthesised from the corresponding $\alpha$ or $\beta$ form of the compound of the formula (VIII).

Synthesis from the corresponding $\alpha$ or $\beta$ isomer of the compound of the formula (VIII) is in general preferred.

It will be appreciated that, when X is NH, Y is CO and n=0 in the compounds of the formulae (I) or (VIII), epimerisation of the CO-ring linkage to the energetically more favourable orientation often takes place readily in the presence of acid or base. In such cases if the less favoured isomer is desired, it is preferred to stereospecifically synthesise the isomer of the compound of the formula (VIII) and to convert it to the required compound of the formula (I) under such conditions to avoid epimersation.

The $\alpha$ or $\beta$ form of the compound of the formula (VIII) may if desired be prepared by known stereospecific processes, such as those leading to the $\alpha$ or $\beta$ isomers of the compound of the formula (VIII) depicted in the Scheme and described in the Descriptions hereinafter.

SCHEME

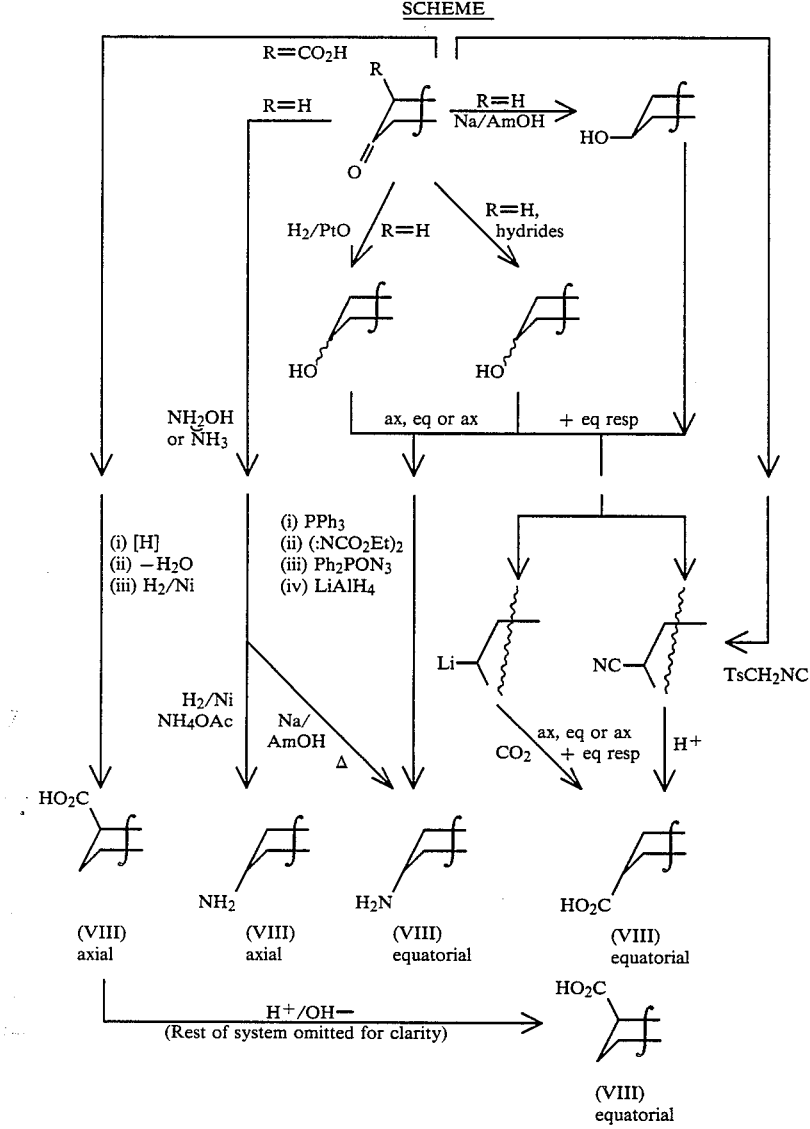

Pharmaceutically acceptable salts, hydrates and N-oxides of the compounds of this invention may be formed conventionally. The salts may be formed for example by reaction of the base compound of formula (I) with a pharmaceutically acceptable organic or inorganic acid.

N-oxides of the nitrogen atom of the bicyclic ring system are produced by reaction of a compound of formula (I) with an organic peracid, such as m-chloroperbenzoic acid in, for example, a chlorinated hydrocarbon solvent at below ambient temperature.

Quaternary ammonium salts may be prepared by reaction of a compound of the present invention with the appropriate alkyl, aryl, aralkyl, chloride, bromide or iodide. This reaction may be carried out in a solvent, such as acetone, methanol, ethanol, dimethylformamide at ambient or elevated temperature with or without pressure.

The compounds of the present invention are dopamine antagonists and may generally be used in the treatment of emesis. Depending on their balance between peripheral and central action on the nervous system, they may also be used in the treatment of disorders relating to impaired gastro-intestinal motility, such as retarded gastric emptying, dyspepsia, flatulence, oesophagal reflux and peptic ulcer and/or in the treatment of disorders of the central nervous system, such as psychosis.

Those compounds of the present invention which are of particular interest for their beneficial effect on gastric motility are the quaternaryammonium salts of such compounds in particular the quaternaryammonium salts of the compounds of formula (I) and also the compounds of formula (III).

The invention also provides a pharmaceutical composition comprising a compound of formula (I), or a pharmaceutically acceptable salt thereof, or an hydrate or N-oxide thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusible solutions or suspensions or suppositories. Orally administerable compositions are preferred.

Tablets and capsules for oral administration are usually presented in a unit dose, and contain conventional excipients such as binding agents, fillers, tabletting agents, lubricants, disintegrants, and wetting agents. The tablets may be coated according to well known methods in the art. Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in the vehicle and filter sterilizing before filling into a suitable vial or ampoule and sealing. Advantageously, adjuvants such as a local anaesthetic, preservatives and buffering agents are also dissolved in the vehicle.

Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound of the invention.

The invention further provides a method of treatment of disorders in mammals, such as humans, which comprises the administration of an effective amount of a compound of the formula (I), or a pharmaceutically acceptable salt thereof, or an hydrate or N-oxide thereof, or a pharmaceutical composition, as hereinbefore defined to the sufferer.

An amount effective to treat the disorders hereinbefore described depends on the relative efficacies of the compounds of the invention, the nature and severity of the disorder being treated and the weight of the mammal. However, a unit dose will normally contain 0.1 to 20 mg for example 0.5 to 10 mg, of the compound of the invention. Unit doses will normally be administered more than once a day, for example 2, 3, 4, 5 or 6 times a day such that the total daily dose is normally in the range 0.01 to 10 mg/kg per day. The compounds of the present invention have the ability to potentiate the effect of conventional analgesics in migraine treatment when administered concurrently with the analgesic.

Accordingly, the present invention also provides a pharmaceutical composition comprising a compound of the formula (I) and an analgesic.

The compound of the formula (I) and the analgesic, such as aspirin or paracetamol, are present in the composition in amounts generally similar to their usual effective dose.

The composition can be a combination product, for example a tablet or capsule containing both a compound of the invention and an analgesic for oral administration, or a twin pack comprising the two active ingredients made up for separate administration.

The invention accordingly provides a method of treatment of migraine comprising the administration of an effective amount of a compound of the formula (I) and an analgesic.

The invention also provides a compound of formula (I), for use in the treatment of emesis, disorders relating to impaired gastro-intestinal motility and of disorders of the central nervous system.

The following examples illustrate the preparation of compounds of the invention and the following descriptions illustrate the preparation of intermediates.

DESCRIPTIONS

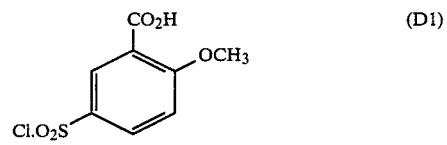

5-Chlorosulphonyl-2-methoxy benzoic acid (D1)

Chlorosulphonic acid (55 ml) was added over 6 hrs at 20° to a stirred mixture of dichloroethane (72 ml), o-anisic acid (26.8 g) and sodium chloride (10 g). The mixture was warmed to 40° and after a further hour warmed to 65°. The mixture was maintained at 65°-70° for 17 hrs, cooled and poured into ice water (300 g) to give the title compound as a colourless solid (28.7 g; 65%).

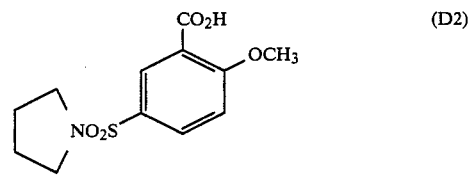

5-Pyrrolidinylsulphonyl-2-methoxybenzoic acid (D2)

5-Chlorosulphonyl-2-methoxybenzoic acid (4.9 g) was added to a solution of pyrrolidine (10 g) in water (150 ml). The solution was stirred for 6 hours, filtered and acidified with dilute hydrochloric acid to yield the title compound as colourless microcrystals (5.27 g; 84%).

NMR δ CDCl₃: 9.87 (broad exchangeable, 1H, CO₂H); 8.45 (doublet, 1H, aromatic 6H); 7.8–8.0 (double doublet, 1H, aromatic 4H); 7.1–7.2 (doublet, 1H, aromatic 3H) 4.0 (s, 3H, OCH₃); 3.35–3.0 (m, 2H, (CH₂)₂—N); 1.7–2.0 (m, 2H, (CH₂)₂—C).

The following were prepared in a similar manner:

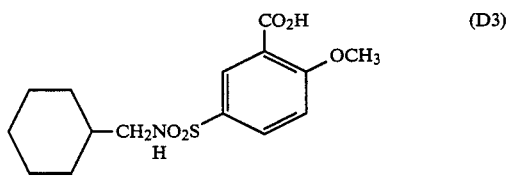

5-N-Cyclohexylmethylsulphamoyl-2-methoxy benzoic acid (D3)

Colourless microcrystals. mp 165° C.

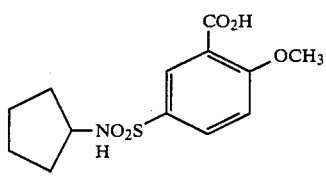 (D4)

5-N-Cyclopentylsulphamoyl-2-methoxy benzoic acid (D4)

Colourless microcrystals. mp 177° C.

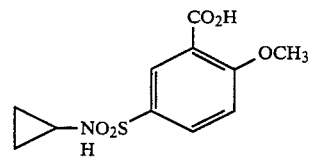 (D5)

5-N-Cyclopropylsulphamoyl-2-methoxy benzoic acid (D5)

Colourless microcrystals. mp 190° C.

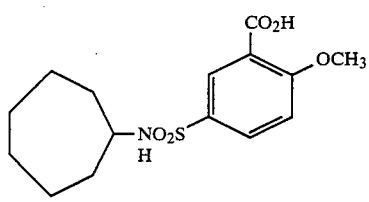 (D6)

5-N-Cycloheptylsulphamoyl-2-methoxy benzoic acid (D6)

Colourless microcrystals. mp 189° C.

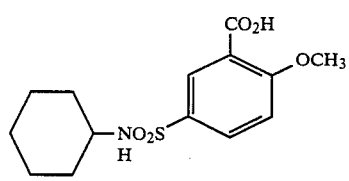 (D7)

5-N-Cyclohexylsulphamoyl-2-methoxy benzoic acid (D7)

Colourless microcrystals. mp 203° C.

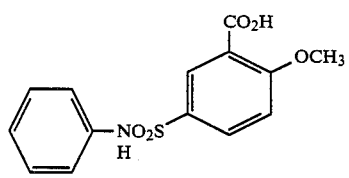 (D8)

5-N-Phenylsulphamoyl-2-methoxybenzoic acid (D8)

Colourless microcrystals. mp 192° C.

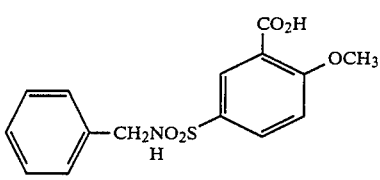 (D9)

5-N-Benzylsulphamoyl-2-methoxybenzoic acid (D9)

Colourless microcrystals. mp 178° C.

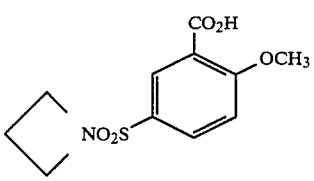 (D10)

3-β-Amino-8-benzyl-8-azabicyclo{3,2,1}octane

Prepared as described in European Patent EP No. 42-705 (Beecham Group Ltd).

D11 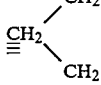 (D11)

5-Azetidinylsulphonyl-2-methoxy benzoic acid (D11)

Colourless microcrystals. ex EtOAc/petrol. p.m.r. (δ CDCl$_3$/d$_6$-dmso).

| 2.07 | m. | 2H | CH$_2$\<CH$_2$/CH$_2$ |
| 3.65 | m. | 4H | CH$_2$\<CH$_2$/CH$_2$—N— |
| 3.95 | s | 3H | Ar—OCH$_3$ |

D12 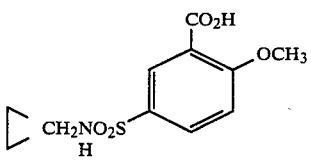 (D12)

5-N-Cyclopropylmethylsulphamoyl-2-methoxy benzoic acid (D12)

Colourless microcrystals. mp 128°.

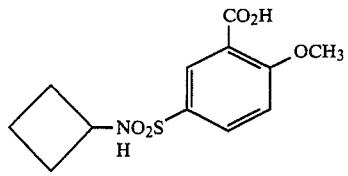

5-N-Cyclobutylsulphamoyl-2-methoxy benzoic acid (D13)

Colourless microcrystals. mp. 173° C.

EXAMPLE 1

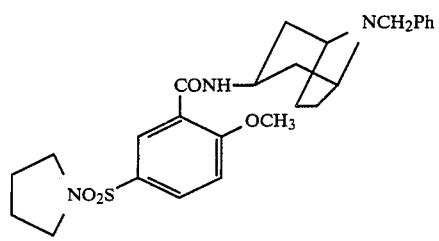

5-Pyrrolidinylsulphonyl-2-methoxy-N-[3β-(8-benzyl-8-azabicyclo{3,2,1}octyl)]benzamide 5-Pyrrolidinylsulphonyl-2-methoxybenzoic acid (D2) (5.22 g, 0.02 mole) was dissolved in anhydrous dimethylformamide (25 ml) containing triethylamine (2.02 g, 2.76 ml) and cooled to 0°. Ethyl chloroformate (2.16 g, 1.96 ml) was added dropwise at 0° over half hour. 3-β-Amino-8-benzyl-8-azabicyclo(3,2,1)octane (D10) (4.2 g) in anhydrous dimethylformamide (15 ml) was added slowly in one portion at 0° and the mixture was allowed to reach ambient temperatures overnight.

The mixture was evaporated to dryness in vacuo, treated with water (15 ml), and 880 ammonia (15 ml) and extracted with chloroform (3×100 ml). The combined organic extracts were dried ($K_2CO_3$) filtered and evaporated in vacuo. The resulting solid was recrystallised from ethylacetate/light petroleum 40°-60° to yield the *title compound* as colourless microcrystals (4.8 g; 50%), mp 178°, analysing as a hemi-hydrate.

$C_{26}H_{34}N_3O_4S$. ½$H_2O$. Required: % C=63.29; H=6.89; N=8.51; S=6.49. Found: % C=63.38, 63.54; H=6.90, 6.73, N=8.34, 8.39; S=6.40, 6.62.

EXAMPLE 2

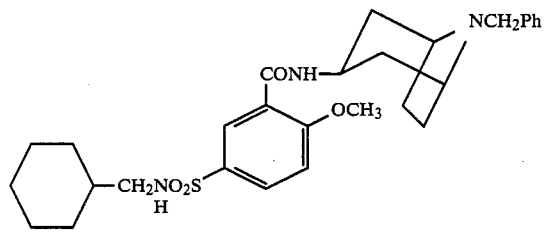

5-N-Cyclohexylmethylsulphamoyl-2-methoxy-N-[3β-(8-benzyl-8-azabicyclo{3,2,1}octyl)]benzamide 5-N-Cyclohexylmethylsulphamoyl-2-methoxy benzoic acid (D3) (3.0 g, 9.2 mmole) was dissolved in anhydrous dimethylformamide (25 ml) containing triethylamine (0.92 g, 1.28 ml). Treatment with ethylchloroformate (1.0 g, 0.88 ml) and 3-β-amino-8-benzyl-8-azabicyclo{3,2,1}octane (D10) (1.98 g) as described in Example 1 and work up via chromatography on Kieselgel 7734 using chloroform as an eluant gave the title compound (2.67 g; 55%) as colourless microcrystals mp 123° C.

$C_{29}H_{39}N_3O_4S$ Calculated $M^+$=525.2661 Observed $M^+$=525.2620 Required: % C=66.29; H=7.43; N=8.00; S=6.10. Found: % C=65.94, 66.04; H=7.43, 7.42; N=7.95, 7.93.

EXAMPLE 3

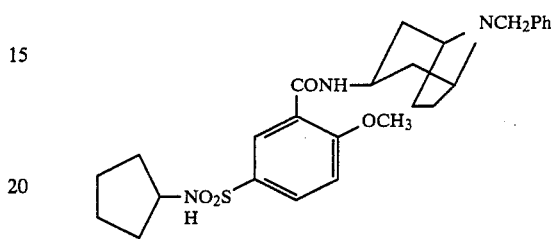

5-N-Cyclopentylsulphamoyl-2-methoxy-N-[3-β-(8-benzyl-8-azabicyclo{3,2,1}octyl)benzamide 5-N-Cyclopentylsulphamoyl-2-methoxy benzoic acid (D4) (3.07 g, 10.3 mmole) was dissolved in anhydrous dimethylformamide (25 ml) containing triethylamine (1.03 g, 1.42 ml). Treatment with ethylchloroformate (1.11 g, 0.98 ml) and 3-β-amino-8-benzyl-8-azabicyclo{3,2,1}octane (D10) (2.22 g) as described in Example 1 gave the title compound (3.67 g; 72%) as colourless microcrystals mp 174° ex ethyl acetate/light petroleum 40°-60°.

$C_{27}H_{35}N_3O_4S$ Calculated $M^+$=497.2346; Observed $M^+$497.2336. Required: % C=65.19; H=7.04; N=8.45. Found: % C=64.81, 64.84; H=7.01, 7.06; N=8.27, 8.29.

Example 4

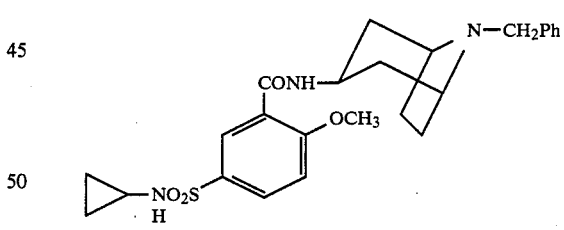

5-N-Cyclopropylsulphamoyl-2-methoxy-N-[3-β-(8-benzyl-8-azabicyclo{3,2,1}octyl)]benzamide 5-N-Cyclopropylsulphamoyl-2-methoxy benzoic acid (D5) (4.0 g, 14.8 mmole) was dissolved in anhydrous dimethylformamide (25 ml) containing triethylamine (1.49 g, 2.04 ml). Treatment with ethylchloroformate (1.60 g, 1.4 ml) and 3-β-amino-8-benzyl-8-azabicyclo{3,2,1}octane (D10) (3.2 g) as described in Example 1 gave the title compound (4.3 g; 62%) as the hemihydrate mp 168° ex ethyl acetate.

$C_{25}H_{31}N_3O_4S$=Calculated $M^+$=469.2035, Observed $M^+$469.2017 Required: % C=62.76; H=6.69; N=8.78 Found: % C=62.92, 62.37; H=6.48, 6.54; N=8.72, 8.77.

EXAMPLE 5

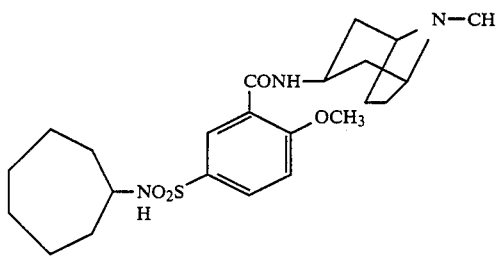

5-N-Cycloheptylsulphamoyl-2-methoxy-N-[3-β-(8-benzyl-8-azabicyclo{3,2,1}octyl)]benzamide 5-Cycloheptylsulphamoyl-2-methoxy-benzoic acid (D6) (1.50 g, 4.6 mmole) was dissolved in anhydrous dimethylformamide (15 ml) containing triethylamine (0.46 g, 0.64 ml). Treatment with ethylchloroformate (0.5 g, 0.44 ml) and 3-β-amino-8-benzyl-8-azabicyclo{3,2,1}octane (D10) (1.0 g) as described in Example 1 gave the title compound. (1.0 g; 42%) purified via chromatography on Kiesgel 7734 and dry ether to give colourless microcrystals, mp 152°–153°.

$C_{29}H_{39}N_3O_4S$ Calculated M+ =525.2661 observed M+ =525.2614 Required: % C=66.29; H=7.43; N=8.00. Found: % C=65.73, 65.47; H=7.59, 7.51, N=7.92, 7.86.

EXAMPLE 6

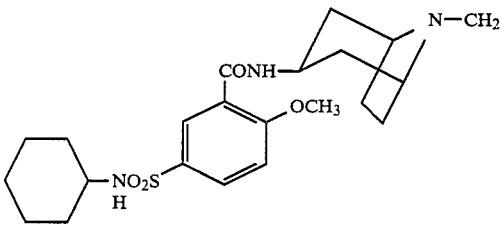

5-N-Cyclohexylsulphamoyl-2-methoxy-N-[3-β-(8-benzyl-8-azabicyclo{3,2,1}octyl)]benzamide 5-N-Cyclohexylsulphamoyl-2-methoxy benzoic acid (D7) (2.50 g, 8.0 mmole) was dissolved in anhydrous dimethylformamide (25 ml) containing triethylamine (0.807 g, 1.1 ml). Treatment with ethylchloroformate (0.87 g, 0.77 ml) and 3-β-amino-8-benzyl-8-azabicyclo{3,2,1}octane (D10) (1.73 g) as described in Example 1 gave the title compound (2.3 g; 56%) as colourless microcrystals mp 142°–143° ex ethyl acetate/light petroleum 40°-60° C.

$C_{28}H_{37}N_3O_4S$ Calculated M+ =511.2585 observed M+ =511.2552. Required: % C=65.75; H=7.24; N=8.22. Found: % C=65.79, 65.41; H=7.34, 7.35; N=8.12, 8.11.

EXAMPLE 7

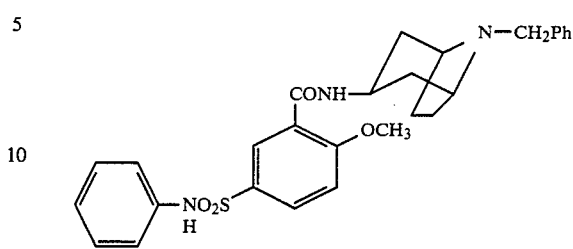

5-N-Phenylsulphamoyl-2-methoxy-N-[3-β-(8-benzyl-8-azabicyclo{3,2,1}octyl)]benzamide 5-N-Phenylsulphamoyl-2-methoxy benzoic acid (D8) (1.5 g, 4.9 mmole) was dissolved in anhydrous dimethylformamide containing triethylamine (0.54 g, 0.47 ml) treatment with ethylchloroformate and 3-β-amino-8-benzyl-8-azabicyclo{3,2,1}octane (1.06 g) as described in Example 1 gave the title compound (1.52 g; 62%) as colourless microcrystals, mp 202°–204° analysing as the hemi-hydrate.

Required: % C=65.37; H=6.23; N=8.17. Found: % C=65.66, 66.01; H=6.10; 6.12; N=8.04, 8.05.

EXAMPLE 8

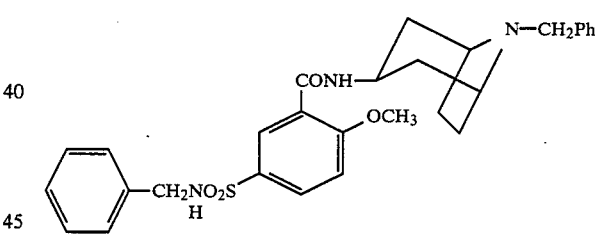

5-N-Benzylsulphamoyl-2-methoxy-N-[3-β-(8-benzyl-8-azabicyclo{3,2,1}-octyl)]benzamide 5-N-Benzylsulphamoyl-2-methoxy benzoic acid (D9) (3.0 g, 9.4 mmole) was dissolved in anhydrous dimethylformamide (30 ml) containing triethylamine (0.94 g, 1.3 ml). Treatment with ethyl chloroformate (0.98 g, 0.87 ml) and 3-β-amino-8-benzyl-8-azabicyclo{3,2,1}octane (D10) (2.02 g) as described in Example 1 gave the title compound (3.57 g; 55%) as colourless microcrystals, mp 165°, purified by chromatography on Kieselgel 7734 via chloroform:methanol (95:5).

$C_{29}H_{33}N_3O_4S$ Calculated M+ =519.2189 observed M+519.2188. Required: % C=67.05; H=6.36; N=8.09. Found: % C=66.76, 66.72; H=6.35, 6,37; N=8.07, 8.01.

EXAMPLE 9

5-N-Cyclopropylmethylsulphamoyl-2-methoxy-N-[3β-benzyl-8-azabicyclo{3.2.1}octyl)]benzamide

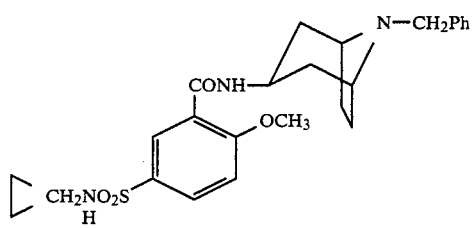

5-N-Cyclopropylmethylsulphamoyl-2-methoxy benzoic acid (D12) (2.85 g, 10 mmole) was dissolved in anhydrous dimethylformamide (30 ml) containing triethylamine (1.01 g, 1.4 ml). Treatment with ethyl chloroformate (1.09 g, 0.96 ml) and 3-β-amino-8-benzyl-8-azabicyclo{3.2.1}octane (D10) (2.16 g) as described in Example 1 gave the *title compound* (3.22 g; 67%) as colourless microcrystals mp 176°–177° purified by column chromatography on Kieselgel 7734 via chloroform:methanol (95:5).

$C_{26}H_{33}N_3O_4S$ Calculated $M^+ = 483.2189$ observed $M^+ = 483.2193$ Required: % C=64.57 H=6.83 N=8.70. Found: % C=64.18 H=7.16 N=8.52.

EXAMPLE 10

5-N-Cyclobutylsulphamoyl-2-methoxy-N-[3β-(8-benzyl-8-azabicyclo{3.2.1}octyl)]benzamide

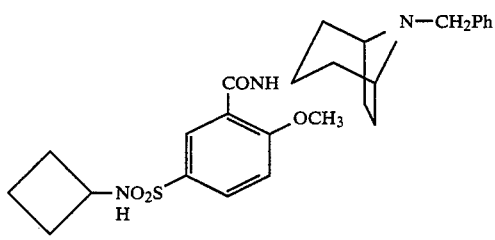

5-N-Cyclobutylsulphamoyl-2-methoxy benzoic acid (D13) (2.85 g, 10 mmole) was dissolved in anhydrous dimethylformamide (30 ml) containing triethylamine (1.01 g, 1.4 ml). Treatment with ethylchloroformate (1.09 g, 0.96 ml) and 3-β-amino-8-benzyl-8-azabicyclo{3.2.1}octane (D10) (2.16 g) as described in Example 1 gave the *title compound* (3.50 g; 73%) as colourless microcrystals mp 150°–151°.

$C_{26}H_{33}N_3O_4S$ Calculated $M^+ = 483.2189$ observed $M^+ = 483.2191$. Required: % C=64.57 H=6.83 N=8.70 S=6.63. Found: % C=64.04 H=6.99 N=8.30 S=6.25.

EXAMPLE 11

5-Azetidinylsulphonyl-2-methoxy-N-{3-β-[8-benzyl-8-azabicyclo(3.2.1)octyl]}benzamide

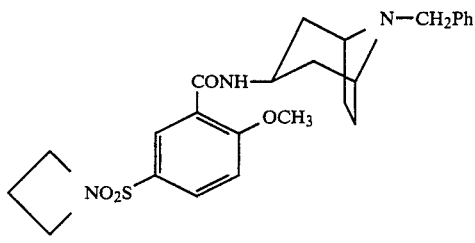

5-Azetidinylsulphonyl-2-methoxy benzoic acid (D11) (2.58 g, 9.5 mmole) was dissolved in anhydrous dimethylformamide (25 ml) containing triethylamine (0.96 g, 1.32 ml). Treatment with ethylchloroformate (1.04 g, 0.92 ml) and 3-β-amino-8-benzyl-8-azabicyclo{3.2.1}octane (D10) (2.06 g) as described in Example 1 gave the *title compound* (3.5 g; 78%) as colourless microcrystals.

$C_{25}H_{31}N_3O_4S$ calculated $M^+=469.2035$, observed $M^+=469.2041$. Required: % C=63.97 H=6.61 N=8.96 S=6.82. Found: % C=63.58 H=6.85 N=8.80 S=7.13.

EXAMPLE 12

5-N-Phenylsulphamoyl-2-methoxy-N'-[3β-(8-methyl-8-azabicyclo(3.2.1)octyl)]benzamide

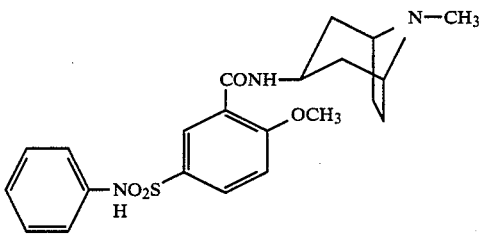

5-N-Phenylsulphamoyl-2-methoxy benzoic acid (D8) (1.5 g, 5 mmol) was dissolved in anhydrous dimethylformamide (25 ml) containing triethylamine (0.54 g, 0.75 ml). Treatment with ethylchloroformate (0.53 g, 0.47 ml) and pseudotropylamine (1.06 g) as described in Example 1, gave the title compound (1.52 g; 62%) as colourless microcrystals, mp 202°–204° analysis as the hemihydrate.

Required: % C=65.37 H=6.23 N=8.17. Found: % C=65.66 H=6.10 N=8.04.

Pharmacological Data

Increase in intragastric pressure

Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for 40 minute period after administration of compound. Student's "t" test was applied to the difference in average values obtained for spontaneous and post compound activity.

The compounds of Examples 1, 5, 6, 7 and 10 were active and the compounds of Examples 4 and 11 slightly active at a dose of 1.0 mg/kg s.c. The compounds of Examples 3 and 9 were active at a dose of 0.5 mg/kg s.c.

Anti-emetic activity in the dog

Compounds were administered subcutaneously 30 minutes prior to administration of a standard dose of apomorphine HCl (0.1 mg/kg subcutaneously) and the vomiting response compared to that obtained when the same animals were dosed with apomorphine HCl and vehicle only.

The compound of Example 3 had an $ED_{50}$ value of 1.0 mg/kg s.c.

The compound of Example 9 had an $ED_{50}$ value of 0.5 mg/kg s.c.

The compounds of Example 1 and 4 had $ED_{50}$ values of 1.0 mg/kg s.c.

The compound of Example 11 had an $ED_{50}$ value of 0.01 mg/kg s.c.

Dopamine Receptor Blocking Activity in the Central Nervous System

Compounds were tested for inhibition of apomorphine induced climbing in the mouse. The test is based on that described by Protais, P., Constantin, J. and Schwartz J. C. (1976), Psychopharmacology, 50, 1–6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—forepaws only on walls; score 2—all paws on wall of cage. The scores at all 3 times and for each mouse are summed and mice drug treated orally compared to mice receiving apomorphine only. A saline only treated group is also included and any score, generally >5% of maximum taken into account.

The compounds of examples 1, 2, 5 and 11 had $ED_{50}$ values of 9.5, 32, 1.2 and 18 mg/kg respectively.

The compounds of examples 4, 8 and 9 were active, active (62% inhibition) and slightly active (23% inhibition) respectively at a dose of 10 mg/kg s.c.

The compounds of examples 2, 6 and 10 were inactive at a dose of 10 mg/kg s.c.

The compound of example 7 was inactive at a dose of 50 mg/kg s.c.

Toxicity

No toxic effects were observed in any of the above tests.

I claim:

1. A compound of the formula:

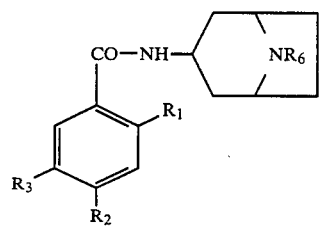

or a pharmaceutically acceptable salt and/or hydrate and/or N-oxide of the nitrogen atom of the bicyclic ring system thereof,
wherein
$R_1$ is $C_{1-6}$ alkoxy;
$R_2$ is hydrogen, chloro, amino or $C_{1-4}$ alkanoylamino; and
$R_3$ is aminosulphonyl N-substituted by one or two $C_{3-8}$ cycloalkyl, $C_{3-8}$ cycloalkyl $C_{1-4}$ alkyl, phenyl or phenyl $C_{1-4}$ alkyl groups, any of which phenyl moieties may be substituted by one or more halogen, trifluoromethyl, $C_{1-6}$ alkoxy or nitro groups, or $C_{3-5}$ polymethylene; and
$R_6$ is $C_{1-7}$ alkyl, —$(CH_2)_sR_7$, s being 0 to 2, and $R_7$ being $C_{3-8}$ cycloalkyl, —$(CH_2)_tR_8$, t being 1 or 2 and $R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolysable acyloxy, wherein said esterified carboxy groups are independently selected from the group consisting of $C_{1-4}$ alkoxycarbonyl, phenoxycarbonyl or benzyloxycarbonyl, either being optionally substituted in the phenyl ring by one or two substituents selected from $C_{1-4}$ alkyl, $C_{1-4}$ alkoxy, trifluoromethyl, halogen or nitro; and wherein said in vivo hydrolysable acyloxy groups are selected from the group consisting of $C_{2-6}$ alkanoyloxy, benzyloxy or benzenesulphonyloxy either being optionally substituted in the phenyl ring by one or two substituents selected from $C_{1-4}$ alkyl, $C_{1-4}$ alkoxy, trifluoromethyl, halogen or nitro, or $C_{1-6}$ alkanesulphonyloxy.

2. A compound according to claim 1, wherein $R_1$ is methoxy and $R_2$ is hydrogen.

3. A compound according to claim 1, wherein $R_3$ is aminosulphonyl monosubstituted by a cyclopentyl, cyclohexyl or cycloheptyl group or N-disubstituted by trimethylene.

4. A compound according to claim 1, wherein $R_1$ is methoxy and $R_2$ is hydrogen and wherein $R_3$ is aminosulphonyl monosubstituted by a cyclopentyl, cyclohexyl or cycloheptyl group or N-disubstituted by trimethylene.

5. A compound according to claim 1, wherein $R_6$ is benzyl optionally substituted in the phenyl ring by one or two substituents selected from $C_{1-4}$ alkoxy, trifluoromethyl, halogen and $C_{1-4}$ alkyl.

6. A compound according to claim 2, wherein $R_6$ is benzyl optionally substituted in the phenyl ring by one or two substituents selected from $C_{1-4}$ alkoxy, trifluoromethyl, halogen and $C_{1-4}$ alkyl.

7. A compound according to claim 3, wherein $R_6$ is benzyl optionally substituted in the phenyl ring by one or two substituents selected from $C_{1-4}$ alkoxy, trifluoromethyl, halogen and $C_{1-4}$ alkyl.

8. A compound according to claim 4, wherein $R_6$ is benzyl optionally substituted in the phenyl ring by one or two substituents selected from $C_{1-4}$ alkoxy, trifluoromethyl, halogen and $C_{1-4}$ alkyl.

9. A pharmaceutical composition for the treatment of emesis or disorders related to impaired gastro-intestinal motility in mammals comprising a pharmaceutically effective amount of a compound according to claims 1, 2, 3, 4, 5, 6, 7 or 8, or a pharmaceutically acceptable salt and/or hydrate and/or N-oxide of the nitrogen atom of the bicyclic ring system thereof and a pharmaceutically acceptable carrier.

10. A method of treatment of emesis or disorders related to impaired gastro-intestinal motility in mammals, which comprises the administration of an effective amount of a compound according to claim 1, or a pharmaceutically acceptable salt and/or solvate and/or N-oxide thereof, to the sufferer.

11. A compound of the formula:

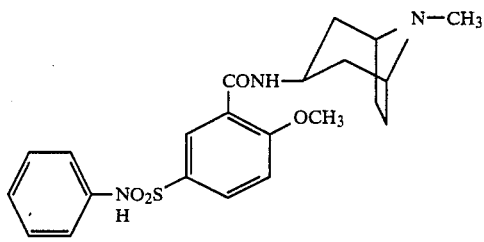

12. A compound selected from the group consisting of:

5-Pyrrolidinylsulphonyl-2-methoxy-N-[3β-(8-benzyl-8-azabicyclo{3.2.1}octyl)]benzamide,
5-N-Cyclohexylmethylsulphamoyl-2-methoxy-N-[3β-(8-benzyl-8-azabicyclo{3.2.1}octyl)]benzamide,
5-N-Cyclopentylsulphamoyl-2-methoxy-N-[3β-(8-benzyl-8-azabicyclo{3.2.1}octyl)]benzamide,
5-N-Cyclopropylsulphamoyl-2-methoxy-N-[3β-(8-benzyl-8-azabicyclo{3.2.1}octyl)]benzamide,
5-N-Cycloheptylsulphamoyl-2-methoxy-N-[3β-(8-benzyl-8-azabicyclo{3.2.1}octyl)]benzamide,
5-N-Cyclohexylsulphamoyl-2-methoxy-N-[3β-(8-benzyl-8-azabicyclo{3.2.1}octyl)]benzamide,
5N-Phenylsulphamoyl-2-methoxy-N-[3β-(8-benzyl-8-azabicyclo{3.2.1}octyl)]benzamide,
5-N-Benzylsulphamoyl-2-methoxy-N-[3β-(8-benzyl-8-azabicyclo{3.2.1}octyl)]benzamide,
Cyclopropylmethylsulphamoyl-2-methoxy-N-[3β-(8-benzyl-8-azabicyclo{3.2.1}octyl)]benzamide,
5-N-Cyclobutylsulphamoyl-2-methoxy-N-[3β-(8-benzyl-8-azabicyclo{3.2.1}octyl)]benzamide,
5-Azetidinylsulphonyl-2-methoxy-N-[3β-(8-benzyl-8-azabicyclo{3.2.1}octyl)]benzamide, and
5-N-Phenylsulphamoyl-2-methoxy-N-[3β-(8-methyl-8-azabicyclo{3.2.1}octyl)]benzamide.

* * * * *